United States Patent
Morrow

(10) Patent No.: US 6,892,567 B1
(45) Date of Patent: May 17, 2005

(54) SYSTEM FOR DETERMING THE INTEGRITY OF A PACKAGE OR PACKAGING MATERIAL BASED ON ITS TRANSMISSION OF A TEST GAS

(76) Inventor: Darrell R. Morrow, 18 Berkshire Dr., Sewell, NJ (US) 08080

( * ) Notice: Subject to any disclaimer, the term of this patent is extended or adjusted under 35 U.S.C. 154(b) by 0 days.

(21) Appl. No.: 10/700,441

(22) Filed: Nov. 3, 2003

Related U.S. Application Data

(62) Division of application No. 09/771,336, filed on Jan. 26, 2001, now Pat. No. 6,640,615.

(51) Int. Cl.$^7$ .......................................... G01N 15/08
(52) U.S. Cl. ....................................................... 73/38
(58) Field of Search .............................. 73/38, 40, 52, 73/49.2, 49.3

(56) References Cited

U.S. PATENT DOCUMENTS

| | | | |
|---|---|---|---|
| 3,590,634 A * | 7/1971 | Pasternak et al. ............. | 374/54 |
| 4,464,927 A * | 8/1984 | Reid ............................. | 73/38 |
| 4,670,847 A * | 6/1987 | Furuse ......................... | 702/51 |
| 4,776,206 A * | 10/1988 | Armstrong et al. ............. | 73/40 |
| 5,065,350 A * | 11/1991 | Fedder ........................ | 702/98 |
| 5,513,515 A * | 5/1996 | Mayer ............................. | 73/38 |
| 5,546,789 A * | 8/1996 | Balke et al. .................... | 73/40 |
| 5,614,718 A * | 3/1997 | Brace .................... | 250/339.13 |
| 5,837,888 A * | 11/1998 | Mayer et al. .................. | 73/38 |
| 5,847,264 A * | 12/1998 | Martin et al. .................. | 73/40 |
| 6,766,682 B2 * | 7/2004 | Engle et al. .................... | 73/38 |
| 2002/0194899 A1 * | 12/2002 | Gebele et al. ................. | 73/38 |
| 2004/0025571 A1 * | 2/2004 | Izutsu et al. .................... | 73/38 |
| 2004/0040372 A1 * | 3/2004 | Plester et al. .................. | 73/38 |

FOREIGN PATENT DOCUMENTS

EP  198950 A2 * 10/1986

OTHER PUBLICATIONS

Leibl et al., Method of non-destructive measurement of the gas permeability of packages, English translation, original appeared in Verpackungsrundschau in 1990.*

* cited by examiner

*Primary Examiner*—Hezron Williams
*Assistant Examiner*—John Fitzgerald

(57) ABSTRACT

A sealed package's transmission of oxygen, water vapor, carbon dioxide, or other gas or vapor that is of interest because of its potential adverse effects on the package contents is determined indirectly, based upon the package's transmission of a different gas selected as a test gas. Helium is preferred as a test gas. The package's total transmission of the test gas is separated into its components of leakage through the package seals and permeation through the packaging material itself. The package's leakage of the gas of interest is determined based on its leakage of the test gas, in accordance with the molecular weights of the gases. The package's permeation of the gas of interest is determined based on its permeation of the test gas, in accordance with data correlating the permeation of the gas of interest and permeation of the test gas for the materials from which the package is made, and with package structure data relating to the size, shape, and disposition of the materials from which the package is made. The package's total transmission of the gas of interest is determined by adding its leakage and permeation components so determined. Such data may be used with other data to determine a packaged product's shelf life or its sensitivity to a gas of interest.

18 Claims, 3 Drawing Sheets

SYSTEM FOR DETERMING THE INTEGRITY OF A PACKAGE OR PACKAGING MATERIAL BASED ON ITS TRANSMISSION OF A TEST GAS

CROSS REFERENCE TO RELATED APPLICATIONS

This application is a division of application Ser. No. 09/771,336 filed on Jan. 26, 2001, now U.S. Pat. No. 6,640,615, and Applicant claims the benefit of the filing date of that application under 35 U.S.C. §§ 120–121.

BACKGROUND OF THE INVENTION

This invention relates to determining the gas or vapor, which may be referred to herein collectively as "gas", transmission properties of packages and materials (for example, films or formed sheets) for use in packages, which may be referred to herein collectively as "packaging". More particularly, this invention relates to determining packaging transmission properties for one gas based upon packaging transmission data for another gas. Still more particularly, this invention relates to, but is not limited to, systems for determining the water vapor, oxygen, and carbon dioxide transmission properties of packaging based upon helium transmission data for such packaging.

Many products manufactured today, such as pharmaceuticals, medical devices and food products, are distributed in sealed packages that are intended to avoid adverse effects on the packaged products that may be caused by exposure to the air and moisture, such as oxidation or hydrolysis of the products, as well as the potential loss (or gain) of volatile components, usually of an organic nature. The packaging process for such products is generally conducted in a controlled atmosphere, such as dry air or an inert atmosphere, intended to preserve the product during storage. Thus, the filled and sealed package contains the product surrounded by the desired atmosphere. Examples of such sealed packages include "blister packs" and envelopes formed from plastic or metal films or multi-layered foils.

Package integrity is often important enough to the safety or utility of the packaged product to warrant testing and measurement, which may be performed during package design and development, packaged product production, and/or packaged product distribution and storage. Desirably, package testing can detect any sealing or other package problem so that it can be remedied quickly, before too many defective packages are produced, thus saving time and money and avoiding distribution of products with substandard packaging.

Package integrity is compromised by gas, or vapor, transmission through the package, which may occur in several ways. Gas transmission may occur by the process of leakage, in which gas travels through passages between interior and the exterior of the package that are large compared to the size of the gas molecules. Because packaging materials tend to be relatively free of holes that are large enough to permit leakage across the material, leakage occurs primarily through the seal areas between the components of the package. Gas transmission may also occur by the process of permeation, in which gas passes through the packaging materials by absorption at one surface of the material, diffusion through the material, and desorption at the other surface of the material. The total gas transmission of a package includes its leakage transmission and its permeation transmission.

Gases which often are of interest in packaging include oxygen, water vapor, and carbon dioxide, as well as other gases or vapors. These gases can have adverse effects on a packaged product and so may be excluded from the controlled atmosphere present when packages are sealed; they are also atmospheric constituents that can enter a sealed package from the surrounding air. Protection of the product from loss of volatile components is also sometimes required of a package. Various methods have been developed to measure the transmission rate of gases and vapors through finished packages or through the materials from which packages are made. One method is gravimetric, in which weight changes due to gas transmission through packaging are measured. For instance, if water vapor transmission rate through a film intended to be used in packaging as a moisture barrier is to be measured, a desiccant can be placed in a cell made of metal or another impervious material having an opening covered by the film to be tested. The cell is weighed and then placed in a high humidity atmosphere. Water vapor flow through the film is absorbed by the desiccant, which maintains a low partial pressure of water vapor inside the cell. Alternatively, water can be in the cell (test fixture) and the test fixture/s stored in a desiccator. The change in weight of the cell over time reflects the total amount of water vapor that has permeated through the film during that time, which when divided by the time yields the water vapor transmission rate. Another method is to place a source of a gas of interest on one side of a sample of a film to be tested, and convey the gas that permeates through the film to a detector that provides quantitative measurements of the gas of interest. Conveyance of permeated gas may be accomplished by passing a carrier gas over the film so as to pick up any gas of interest that has permeated through the film and carry it to the detector; such a carrier gas is selected so that the detector is not responsive to it or so that its effects on the detector can be distinguished from those of the gas of interest. Conveyance of permeated gas may also be accomplished by a vacuum pump disposed to draw permeated gas to the detector. Examples of detectors that have been used in this method include mass spectrometers, gas chromatographs, and infrared detectors.

The above-described prior art methods of determining gas transmission properties of packaging have various drawbacks. They are primarily suited to determining gas transmission properties of packaging materials, rather than packages, but it is often the performance of completed packages that is primarily of interest. They are often slow; it may take days, weeks, or months for the packaging materials to transmit enough gas of interest to obtain a significant response from the detector. Their sensitivity may be low, so that they may be unable to measure transmission rates for packaging materials with low gas transmission rates. It is expensive to carry out the measurement methods of the prior art; not only is expensive equipment required, but different equipment is required for each gas of interest, and low throughput makes the cost per measurement high. It is therefore a general object of the present invention to provide methods and apparatus for easily, quickly, accurately and relatively inexpensively determining packaging leakage and permeation of gases of interest, including, but not limited to, oxygen, water vapor, and carbon dioxide.

BRIEF SUMMARY OF THE INVENTION

In accordance with one aspect of the present invention, data is obtained as to the total transmission rate of a test gas through a package. The test gas permeation rate of the package is determined based upon test gas permeation data for the materials from which the package is made and the geometry of the package. The test gas leakage rate of the package is determined by subtracting the determined test gas permeation rate from the test gas total transmission rate. Having determined the leakage and permeation components of the total gas transmission rate for the test gas, the leakage rate for a gas of interest can be determined based upon the leakage rate for the test gas, the permeation rate for the gas of interest can be determined based upon the permeation rate for the test gas, and the total transmission rate for the gas of interest can be determined by adding the determined leakage and permeation rates for the gas of interest. Helium is preferred as a test gas, i.e. helium transmission data is preferred as test gas transmission data. The invention may be implemented using a computer operating on test gas and gas-of-interest leakage and/or permeation data for the materials from which a package is constructed, package structure data, and test gas total transmission rate data to determine the package gas transmission properties for the gas of interest. By obtaining data enabling correlation of leakage and permeation properties of test and other gases of interest, data from a single measurement of a package's total test gas transmission rate enables determination of the leakage and permeation rates of many gases of interest. Similarly, multigas permeation data can be obtained for permeable films and formed sheets. Further in accordance with the invention, the transmission rates determined for the gas or gases of interest may be used with other package-related data to determine properties such as shelf life of a packaged product or sensitivity of a product to gases of interest.

The oxygen, water vapor, carbon dioxide, and other gas-of-interest transmission properties of a packaging material such as a formed sheet are also often of interest. Therefore, in accordance with another aspect of the invention, data is obtained as to the transmission rate of a test gas through a specimen of the packaging material, and the specimen's permeation of the gas of interest is determined based on its permeation of the test gas, in accordance with data correlating the permeation of the gas of interest and permeation of the test gas for the packaging material.

These and other objects and features of the present invention are set forth in greater detail in the following description and the drawings.

DETAILED DESCRIPTION

In accordance with the present invention, a package's (or packaging material's) transmission of a gas of interest is determined indirectly, based upon data obtained from measurement of the package's (or packaging material's) transmission of a different gas selected for use as a test gas.

Figure 1:
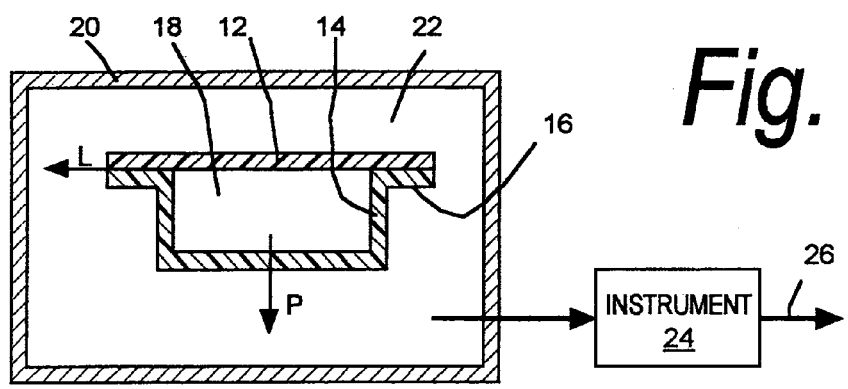
FIG. 1 is a schematic diagram of a testing system that can be used to measure the total gas transmission rate of a package.

FIG. 1 is a schematic diagram illustrating a testing system that can be used to measure the total gas transmission of a package. The system of FIG. 1 per se is part of the prior art; it is included in the present application to illustrate the type of system that can be used to obtain data used in the present invention. The package shown is a blister pack formed from a pair of sheets of packaging material 12 and 14. Sheet 14 includes a well or blister for receiving a product to be packaged, the well being surrounded by a peripheral portion forming a sealing flange 16. The sheet 12 of lidding material overlies the sheet 14 to define an interior space 18 between the well or blister portion of sheet 14 and the lidding sheet 12. Sheet 12 is adhered to sheet 14 where it contacts the peripheral flange 16 in a manner intended to seal the interior space 18, including the package contents and the atmosphere present when the package was formed, from the outside atmosphere. Sheets 12 and 14 may be made of plastic or metal/plastic film or foil or similar laminated/layered materials.

To facilitate testing of the package, a gas (which is sometimes referred to as a tracer gas but will be referred to herein as a test gas) may be incorporated in the controlled atmosphere present during the packaging process or introduced post-sealing, the test gas being chosen to be relatively easily detected upon transmission from the package. The package is placed in a fixture 20 having a closed chamber 22 connected to an instrument 24 that is quantitatively responsive to the test gas. Helium is commonly used as the test gas, instrument 24 may be a mass spectrometer, and chamber 22 may be evacuated during a test. The instrument 24 measures the amount of test gas emanating from the package during the test, and provides output data 26 representing the amount of test gas transmitted, the test gas transmission rate, or both.

The gas transmission measured by the system of FIG. 1 includes two components. One component is due to permeation, indicated by the arrow labeled "P", in which gas passes through sheet 12 or 14 by absorption or dissolution at the interior surface of the sheet from interior space 18, diffusion through the sheet, and desorption or evaporation from the exterior surface. The other component is due to leakage, indicated by the arrow labeled "L", in which gas travels through passages between interior space 18 and the exterior of the package that are large compared to the size of the gas molecules. Packaging materials tend to be relatively free of holes that are large enough to permit leakage across the material, and so leakage occurs primarily through the seal area between the sheets 12 and 14 at the periphery 16 of the package.

Figure 2:
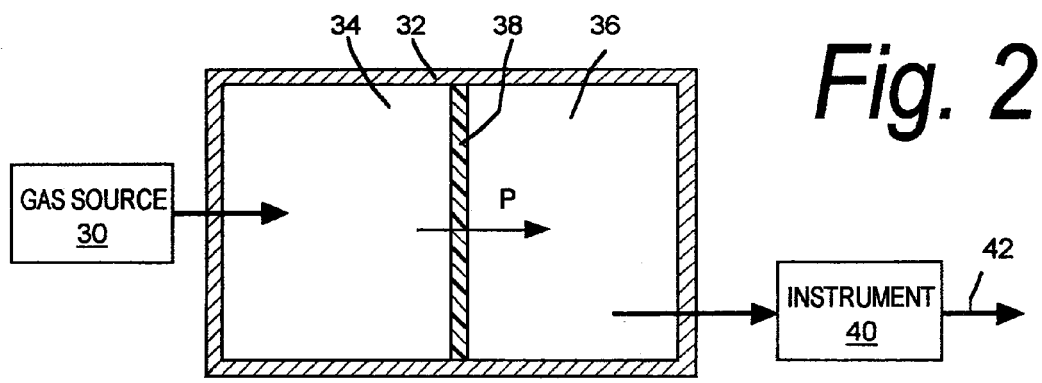
FIG. 2 is a schematic diagram of a testing system that can be used to measure the permeation rate of a packaging material, or formed sheet.

FIG. 2 is a schematic diagram of a testing system that can be used to measure the permeation of a gas through a packaging material. The system of FIG. 2 is also part of the prior art, and like FIG. 1 is included in the present application to illustrate the type of system that can be used to obtain data used in the present invention. A sheet 38 of packaging material—formed or unformed—to be tested is placed in a test fixture 32 so as to divide the interior of the fixture 32 into a first chamber 34 and a second chamber 36. A gas source 30 is coupled to first chamber 34. An instrument 40 responsive to the source gas is coupled to second chamber 36. Instrument 40 measures the amount of source gas that permeates from first chamber 34 through the sheet 38 into second chamber 36 during the test, illustrated by the arrow labeled "P", and provides output data 42 representing the amount of source gas transmitted, the source gas transmission rate, or both.

The system of FIG. 1 is well suited to measuring gas transmission through completed packages, but usually only for gases that can be incorporated into completed packages as tracer or test gases and whose transmission rates from such packages can be accurately measured. The system of FIG. 2 is well suited to measuring gas permeation through packaging materials, including formed sheets, as long as the dimensions of the material samples are great enough, and it can be used with different gases of interest. However, it can be expensive and time-consuming to make such measurements, and the system of FIG. 2 often cannot be used reliably to measure gas transmission from a completed package.

Figure 3:
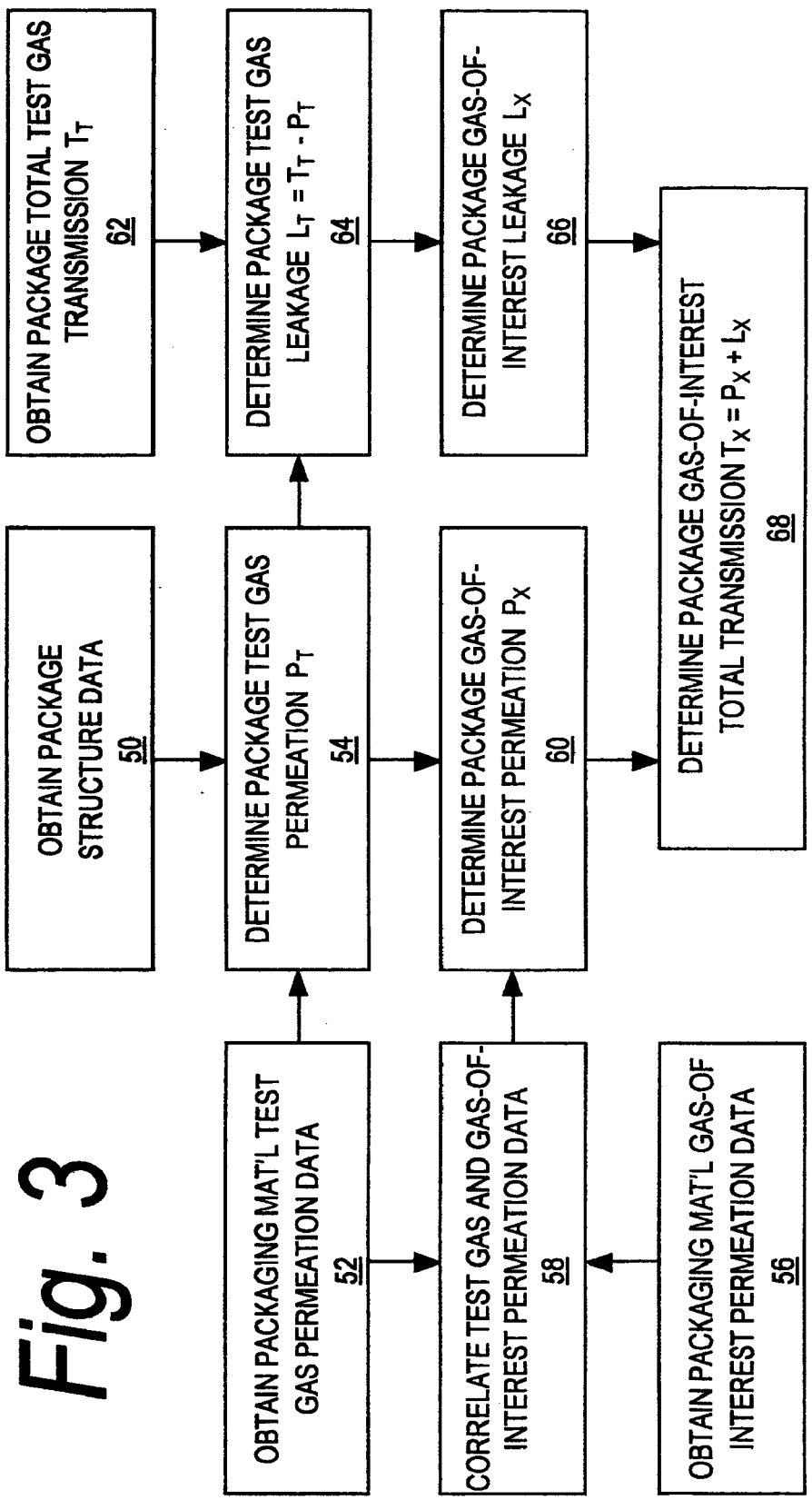
FIG. 3 is a flow diagram of a method according to the present invention for determining a package's transmission of a gas of interest based upon measurement of the package's transmission of a test gas.

Although it is not reasonably feasible to use the system of either FIG. 1 or 2 by itself to measure the permeation, leakage, and/or total transmission of an atmospheric gas of interest through a completed package, Applicant has determined that the desired information can be determined based on data of the type obtained from these systems. FIG. 3 is a flow diagram of a method for doing so in accordance with the present invention.

The invention is based upon the recognition that the gas transmission of a package can be separated into permeation and leakage components, and that the permeation and leakage properties for one gas can be determined empirically based on the permeation and leakage properties for another gas. In the following discussion and in the drawings, the symbol T will be used to represent total gas transmission, L will be used to represent leakage, and P will be used to represent permeation; the subscript T will be used to refer to a test gas, and the subscript X will be used to refer to another gas of interest. While steps may be discussed sequentially in the following discussion, that does not mean that such steps must be performed in the sequence discussed. The following discussion involves data gathering and data manipulation steps. Data is referred to as being "obtained" to indicate that it is made available for use in the processes described. While such data may be obtained by a measurement made in the course and for the purpose of carrying out the invention, that is not necessarily the case, and the present invention may involve determinations made using stored or recorded data measured or derived from measurements made in other contexts. In the following discussion and in the drawings, desired information is "determined" by manipulating the data or information obtained in the antecedent steps to generate data representing the desired information.

Turning to FIG. 3, in step 62, a package's total transmission of a test gas is obtained. This quantity, $T_T$, may be obtained for instance by measurement in a test system as illustrated in FIG. 1 using helium as a test gas and a calibrated mass spectrometer as a measuring instrument. The test gas total transmission $T_T$ is composed of a leakage component $L_T$ and a permeation component $P_T$, i.e. $T_T=L_T+P_T$. The system of FIG. 1 is unable to distinguish these components. However, they can be distinguished by the process shown in steps 50, 52, 54, and 64. In step 50, data is obtained regarding the structure of the package under test. This data includes the identity of the packaging materials from which the package was formed, such as the identity of sheets 12 and 14 of the blister pack shown in FIG. 1, as well as the shape and dimensions of the package. In step 52, test gas permeation data is obtained for each of the packaging materials from which the package was formed. Such test gas permeation data may be obtained by measurement using a test system such as that illustrated in FIG. 2, again for instance using helium as a test gas and a calibrated mass spectrometer as a measuring instrument. The test gas permeation data may be the permeability of the packaging material, i.e. the test gas permeation rate per unit area of packaging material per unit partial differential pressure of test gas, at specified temperature and other conditions. In step 54, the test gas permeation of the package under test, $P_T$, is determined from the data obtained in steps 50 and 52. The test gas permeation through each component of the package is determined from the area of the component exposed to the package's interior product-containing space and the test gas permeation data for the packaging material from which the component is constructed. The test gas permeation through the entire package is determined as the sum of the permeation rates through each of its components. Thus, for example, if a package is made of components 1 and 2 having test gas permeabilities $p1_T$ and $p2_T$ and areas A1 and A2, the test gas permeation $P1_T$ through component 1 is determined as $P1_T=p1_T*A1$, the test gas permeation $P2_T$ through component 2 is determined as $P2_T=p2_T*A2$, and the package test gas permeation is determined as $P_T=P1_T+P2_T$. (For layered components, the "parallel elements equation" applies; for instance, the permeability p of a component having layers a, b, c, ... with respective permeabilities $p_a$, $p_b$, $p_c$, ... may be determined as $1/p=1/p_a+1/p_b+1/p_c+ \ldots$) Having determined $P_T$, in step 64 the test gas leakage component $L_T$ is determined by subtracting the test gas permeation component $P_T$ determined in step 54 from the total test gas transmission $T_T$ obtained in step 62, i.e. $L_T= T_T-P_T$.

Having segregated the leakage and permeation components of test gas transmission, leakage and permeation $L_X$ and $P_X$ of another gas of interest such as oxygen, water vapor, or carbon dioxide can be determined. In step 66 the package's gas-of-interest leakage $L_X$ is determined from the package's test gas leakage $L_T$. This may be determined based on the square root of the ratio of the molecular weight of the test gas $M_T$ and the molecular weight of the gas of interest $M_X$, as $L_X=L_T (M_T/M_X)^{1/2}$ (or equivalently, based upon the ratio of the square roots of the molecular weights). Determining the gas-of-interest permeation $P_X$ from the test gas permeation $P_T$ can be done empirically, in the manner set forth in steps 56, 58, and 60, using test gas permeation data obtained in step 52. In step 56, gas-of-interest permeation data is obtained for each of the packaging materials from which the package was formed. Such gas-of-interest permeation data may be obtained using a test system such as that illustrated in FIG. 2, using an instrument 40 that is suited to measuring the gas of interest. In step 58, the gas-of-interest permeation data and the test gas permeation data are correlated, that is, organized in a manner so that a packaging material's permeation of one gas can be obtained from its permeation of another gas. In step 60, the package's gas-of-interest permeation $P_X$ is determined from the package's test gas permeation $P_T$ and the correlated gas-of-interest and test gas permeation data. Thus, for example, if a package is made of components 1 and 2 having test gas permeabilities $p1_T$ and $p2_T$, gas-of-interest permeabilities $p1_X$ and $p2_X$, and contributions $P1_T$ and $P2_T$ to the total package test gas permeation, then the contributions $P1_X$ and $P2_X$ to the total package gas-of-interest permeation can be determined based on the permeability ratios as $P1_X = P1_T (p1_X/p1_T)$ and $P2_X = P2_T (p2_X/p2_T)$, and the total package gas-of-interest permeation can be determined as $P_X = P1_X + P2_X$.

Having determined the package's gas-of-interest permeation $P_X$ in step 60 and its gas-of-interest leakage $L_X$ in step 66, its total gas-of-interest transmission $T_X$ can be determined in step 68 as $T_X = P_X + L_X$. It should be noted that knowledge of the relative contributions of permeation and leakage to the overall gas transmission for a package can be used to identify, for those cases where the transmission rate is too high, which type of remedy is needed. Improved gas/vapor barrier performance is accomplished by different approaches depending on whether the operative mechanism is permeation-based or leakage-based.

It can be seen in the foregoing example that correlating step 58 can be implemented in several equivalent ways. For instance, it can be implemented by storing each piece of permeability data in association with data identifying the gas and the material to which it pertains, such as by storing the data in a table or in a database. Then, data representing the permeability of a package component's material to the test gas and to the gas of interest would be obtained, data representing the package component's permeation of the test gas would be obtained, and these data would be multiplied and divided in any convenient order to determine the permeation of the gas of interest through the package component. In the example, $P1_T$ and $p1_X$ would be obtained by locating the stored data elements associated with material 1 and gases T and X, $P1_T$ would be obtained, and these data operated on by any convenient sequence of multiplication and division steps to produce the quantity $P1_T (p1_X/p1_T)$. Another way of implementing the correlating step 58 is to store a correlating function of the permeation data, such as the permeability ratio, in association with data identifying the material and the gases to which it pertains. In the example, data representing the ratio $(p1_X/p1_T)$ would be obtained by locating the stored data element associated with material 1 and gases T and X, $P1_T$ would be obtained, and these data multiplied to produce the quantity $P1_T (p1_X/p1_T)$. Other variations might be employed, for instance when the permeabilities are not single valued but are functions of some other variable, such as temperature. In such circumstances, data representing the function can be stored for each material and gas, and each material's function can be evaluated for the test gas and conditions and for the gas and conditions of interest. In every case, the permeation of a test gas and some other gas of interest through a package component are related, so that the gas-of-interest permeation can be expressed as some function of the test gas permeation, e.g. $P_X = f(P_T)$. All that is required of the correlating step is that data relating to the test gas and gas of interest permeabilities are stored in a way that enables the function to be evaluated; data so stored provides correlating data for use in evaluating the function. A similar correlating step is implicitly involved in determining the gas-of-interest leakage from the test gas leakage in step 66, and data representing the molecular weights of the gases, their ratio, their square roots, or the ratio of their square roots can be organized and stored as leakage correlation data for use in evaluating the function $L_X = L_T (M_T/M_X)^{1/2}$ or its equivalent.

The present invention has several advantages compared to prior art methods involving directly measuring package transmission of atmospheric gases of interest or inferring package performance based on measuring the permeation of atmospheric gases of interest through the packaging materials. One advantage is speed. For example, one prior art method of testing packages for water vapor transmission is to place a large number of sample packages in a high humidity chamber and remove samples at periodic intervals to measure the amount of water inside the package. With typical water vapor transmission rates, it may take unacceptably long periods of time to obtain significant data from such testing, and such delay greatly reduces the usefulness of the data for package design or quality control purposes. Other methods and instrumentation, while faster, may not be of sufficient sensitivity to enable high barrier materials or seals to be characterized. Other advantages are sensitivity of measurements and reliability of results. The test gas of the present invention can be chosen for ease of incorporation in a package and ease and accuracy of detection during package testing. Helium is inert and can be easily incorporated as a tracer gas in packages with no ill effects on the packaged products, and can be accurately detected and distinguished from other gases using commercially available instruments, and can be accurately detected in sufficiently small quantities that reliable helium transmission test results can be obtained in a relatively short amount of time and for very low transmission rates. With the method of the present invention, a packaging material—formed or unformed—can be subjected once to careful and accurate permeation testing for a test gas and other gases of interest, using test methods and apparatus and a length of time that is sufficient to produce data of the scope and accuracy that is desired. For instance, large areas of packaging materials, substantially larger than the areas in typical packages, may be tested to increase the quantity of transmitted gas to be measured, thereby enabling increased measurement accuracy, reduced measurement time, or both. The results of such testing can be stored and used at any later time to generate information applicable to a gas of interest from data obtained using a test gas.

The latter aspect is a particularly significant aspect of the present invention. The steps of manipulating pertinent data to obtain the desired information regarding a particular package's transmission of some gas of interest can be entirely separated from the data gathering steps, and the underlying data gathering steps whose results are used need not have been undertaken with the specific intention of obtaining that desired information regarding a particular package. Thus, a program of packaging material testing may be undertaken to determine the permeation characteristics of a number of different packaging materials, any of which might be used in some package of interest, with respect to a number of different gases, any of which might be used as a test gas or considered to be a gas of interest in the future. The results of such testing may be embodied as stored data accessible by a computer, for instance as database elements, lookup table components, or correlating functions such as permeability ratios. Once obtained and stored, the data representing the results of such testing can be used to determine the permeation of any gas through any packaging materials represented in the data set. Similarly, the package structure data can, but need not, be obtained by measurement in connection with obtaining desired information regarding a particular package's transmission of some gas of interest. For instance, package structure data can be obtained from package design documentation.

Figure 4:
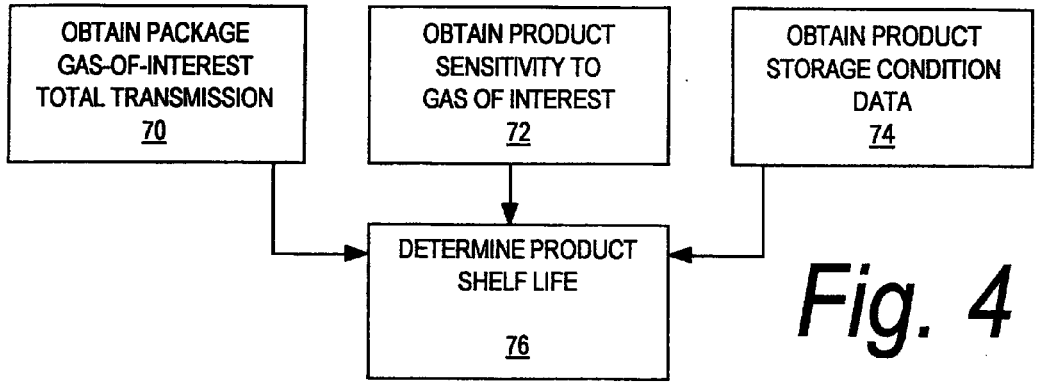
FIG. 4 is a flow diagram of a method according to the present invention for determining a packaged product's shelf life based upon the package's transmission of a gas of interest.
Figure 5:
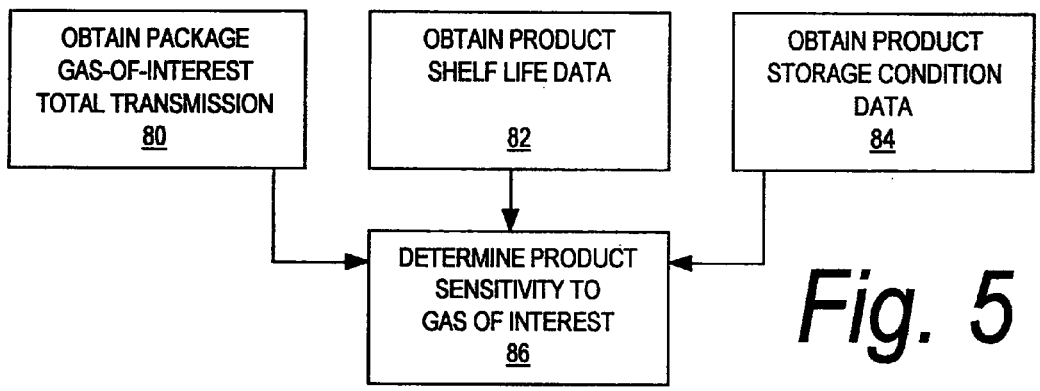
FIG. 5 is a flow diagram of a method according to the present invention for determining a packaged product's sensitivity to a gas of interest based upon the packaged product's shelf life.

The information determined by the methods illustrated in FIG. 3 can be used for additional purposes, as illustrated in the flow diagrams of FIGS. 4 and 5. FIG. 4 is a flow diagram of a method according to the present invention for determining a packaged product's shelf life based upon other information including the package's transmission of a gas of interest. In step 70, a package's total transmission rate of a gas of interest is obtained. This information may be determined by a method according to FIG. 3, or obtained by some other method. In step 72, information is obtained regarding the packaged product's sensitivity to the gas of interest. For instance, a packaged food product may be deemed stale if it has absorbed a certain amount of water vapor, or a packaged pharmaceutical product may be considered to be unacceptably degraded if it has been oxidized to a certain extent. A medical product may be deemed non-sterile because the leak rate is too high, suggesting leakage pathways large enough to allow microbial ingress. In step 74, information is obtained regarding the conditions to which the packaged product is expected to be exposed during storage, including the amount of the gas of interest in the atmosphere surrounding the package. In step 76, the packaged product's shelf life is determined based upon the package's total transmission rate of the gas of interest obtained in step 70, the packaged product's sensitivity to the gas of interest obtained in step 72, and the storage condition data obtained in step 74.

FIG. 5 is a flow diagram of a method according to the present invention for determining a packaged product's sensitivity to a gas of interest based upon other information including the package's transmission of a gas of interest. In step 80, a package's total transmission rate of a gas of interest is obtained. This information may be determined by a method according to FIG. 3, or obtained by some other method. The packaged product's shelf life under particular conditions is obtained in step 82. For example, a number of samples of packaged food product may be exposed to environmental conditions including the gas of interest, and samples may be periodically tested to determine whether the packaged product has been preserved in an acceptable condition; when tested samples become unacceptable, the time of exposure prior to testing may be deemed the shelf life under the test conditions. In step 84, information is obtained regarding the conditions to which the packaged product was exposed during the test, including the amount of the gas of interest in the atmosphere surrounding the package. In step 86, the packaged product's sensitivity to the gas of interest is determined based upon the package's total transmission rate of the gas of interest obtained in step 80, the packaged product's shelf life obtained in step 82, and the storage condition data obtained in step 84.

Figure 6:
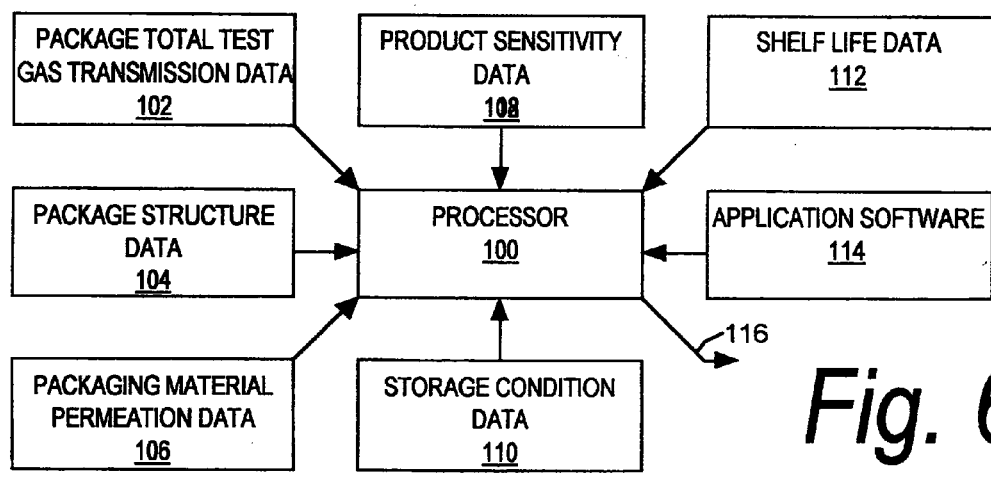
FIG. 6 is a block diagram of a system according to the present invention for carrying out the methods of FIGS. 3, 4, and/or 5.

FIG. 6 is a block diagram of a system according to the present invention that can be used to carry out the methods of FIGS. 3, 4, and/or 5. The system is a computer system having a processor 100, and software 114 enabling the processor to carry out the methods of FIGS. 3, 4, and/or 5 as described herein to produce output data 116 representing the results of the determinations as described herein. The system includes stored data accessible by processor 100 for use in the described methods. The stored data may include package total test gas transmission data 102, package structure data 104, and packaging material permeation data 106, which enable the system to make the determinations described with respect to FIG. 3. If the stored data includes product sensitivity data 108 and package storage condition data 110, the system can make the shelf life determination described with respect to FIG. 4. If the stored data includes package storage condition data 110 and packaged product shelf life data 108, the system can make the product sensitivity determination described with respect to FIG. 5.

The system of FIG. 6 may be implemented in an ordinary computer such as a PC, operated by a single entity that performs measurements to obtain the required input data and operates the computer to generate the desired output information. However, it should be understood that the data gathering, storage, and processing steps of the present invention can be distributed in space and time.

As has been noted, there are circumstances in which it may be desired to determine the oxygen, water vapor, carbon dioxide, or other gas-of-interest transmission of a specimen of packaging material. For instance, it may be desired for quality control purposes to determine the gas-of-interest transmission of the well of a blister pack (such as the well portion of sheet 14 shown in FIG. 6) selected for testing, perhaps in the course of inspecting formed sheets prior to their use in packaging products or inspecting finished product-containing packages. As previously noted, most packaging materials are leak free, and their gas transmission may be expected to be entirely due to permeation. Because the permeation rate of oxygen, water vapor, carbon dioxide, and other atmospheric gases through typical packaging materials is so low, the area of an individual blister is so small, and the sensitivity of existing instruments which directly detect these gases is so low, direct measurement of the permeation of a gas of interest through an individual blister may be impractical for quality control purposes due to the length of time that would required for a measurable amount of gas to permeate through it. However, because the helium permeability of packaging materials is substantially higher than their atmospheric gas permeability and because of the high sensitivity of existing helium measuring instruments, accurate helium permeation measurements can be made quickly enough for practical use even with small specimens of packaging material such as an individual blister. In accordance with the present invention the gas-of-interest permeation may be determined indirectly for such specimens based on test gas permeation data using essentially the method shown in steps 52, 54, 56, 58, and 60 in FIG. 3 and described above. The test gas permeation $P_T$ for a specimen of packaging material may be obtained by measurement using a test gas such as helium in apparatus as illustrated in FIG. 2. Test gas and gas-of-interest permeation data for the packaging material of which the specimen is made are obtained and correlated as described above with respect to steps 52, 56, and 58, and the specimen's gas-of-interest permeation $P_X$ is determined from the package's test gas permeation $P_T$ and the correlated gas-of-interest and test gas permeation data as described above with respect to step 60. Thus, for example, for a specimen made of a packaging material having test gas permeability $P_T$ and gas-of-interest permeability $p_X$, the specimen's gas-of-interest permeation can be determined based on the test gas permeation and the test gas and gas-of-interest permeabilities as $P_X = P_T (p_X/p_T)$. This determination can be made using apparatus as shown in and described with respect to FIG. 6.

While particular embodiments of the invention have been described, variations no doubt will occur to those skilled in the art without departing from the spirit and scope of the invention.

What is claimed is:

1. A method of determining the effect of a gas of interest on a product within a package comprising the steps of:
   a. obtaining data representing the package's total transmission of a test gas, said test gas being different than said gas of interest;
   b. determining the package's transmission of the gas of interest based upon its test gas transmission;
   c. obtaining storage condition data representing the amount of the gas of interest in the atmosphere surrounding the package during storage; and d. obtaining data representing the sensitivity of the product to the gas of interest and determining the shelf life of the packaged product based upon the package's gas-of-interest transmission, the storage condition data, and the product sensitivity data, or obtaining data representing the shelf life of the packaged product and determining the sensitivity of the product to the gas of interest based upon the package's gas-of-interest transmission, the storage condition data, and the shelf life data.

2. The method of claim 1, wherein step b includes:

determining the package's test gas leakage and test gas permeation components of said total test gas transmission; and determining the package's transmission of the gas of interest based upon its test gas transmission and a correlation between test gas and gas-of-interest transmission.

3. The method of claim 1, wherein step d includes obtaining data representing the sensitivity of the product to the gas of interest and determining the shelf life of the packaged product based upon the package's gas-of-interest transmission, the storage condition data, and the product sensitivity data.

4. The method of claim 3, wherein the product is a food product, a medical product, or a pharmaceutical product.

5. The method of claim 3, wherein the test gas is helium.

6. The method of claim 3, wherein the gas of interest is oxygen, water vapor, or carbon dioxide.

7. The method of claim 1, wherein step d includes obtaining data representing the shelf life of the packaged product and determining the sensitivity of the product to the gas of interest based upon the package's gas-of-interest transmission, the storage condition data, and the shelf life data.

8. The method of claim 7, wherein the product is a food product, a medical product, or a pharmaceutical product.

9. The method of claim 7, wherein the test gas is helium.

10. The method of claim 7, wherein the gas of interest is oxygen, water vapor, or carbon dioxide.

11. Apparatus for determining the effect of a gas of interest on a product within a package, the apparatus comprising stored data and a processor operating on the stored data in accordance with software, wherein the stored data includes data representing the package's total transmission of a test gas, the test gas being different than the gas of interest, storage condition data representing the amount of the gas of interest in the atmosphere surrounding the package during storage, and data representing the sensitivity of the product to the gas of interest, and the processor operates on the test gas transmission data to determine the package's transmission of the gas of interest, and the processor operates on the gas-of-interest transmission data, the storage condition data, and the product sensitivity data to determine the shelf life of the packaged product.

12. The apparatus of claim 11, wherein the data pertaining to a test gas pertains to helium.

13. The apparatus of claim 11, wherein the data pertaining to a gas of interest includes data pertaining to oxygen, water vapor, or carbon dioxide.

14. The apparatus of claim 11, wherein the data pertaining to a product includes data pertaining to a food product, a medical product, or a pharmaceutical product.

15. Apparatus for determining the effect of a gas of interest on a product within a package, the apparatus comprising stored data and a processor operating on the stored data in accordance with software, wherein the stored data includes data representing the package's total transmission of a test gas, the test gas being different than the gas of interest, storage condition data representing the amount of the gas of interest in the atmosphere surrounding the package during storage, and data representing the sensitivity of the product to the gas of interest, and the processor operates on the test gas transmission data to determine the package's transmission of the gas of interest, and the processor operates on the gas-of-interest transmission data, the storage condition data, and the shelf life data to determine the sensitivity of the product to the gas of interest.

16. The apparatus of claim 15, wherein the data pertaining to a test gas pertains to helium.

17. The apparatus of claim 15, wherein the data pertaining to a gas of interest includes data pertaining to oxygen, water vapor, or carbon dioxide.

18. The apparatus of claim 15, wherein the data pertaining to a product includes data pertaining to a food product, a medical product, or a pharmaceutical product.

* * * * *